(12) United States Patent
Montaño et al.

(10) Patent No.: US 11,034,950 B2
(45) Date of Patent: Jun. 15, 2021

(54) DELIVERING ENZYME USING AN INJECTABLE HYDROGEL DEPOT

(71) Applicant: Saint Louis University, St. Louis, MO (US)

(72) Inventors: Adriana M. Montaño, St. Louis, MO (US); Silviya Petrova Zustiak, St. Louis, MO (US); Era Jain, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 117 days.

(21) Appl. No.: 16/179,158

(22) Filed: Nov. 2, 2018

(65) Prior Publication Data
US 2019/0127726 A1    May 2, 2019

Related U.S. Application Data

(60) Provisional application No. 62/580,699, filed on Nov. 2, 2017.

(51) Int. Cl.
| | |
|---|---|
| *C12N 11/04* | (2006.01) |
| *A61K 47/69* | (2017.01) |
| *A61M 5/178* | (2006.01) |
| *A61K 47/10* | (2017.01) |
| *A61K 9/00* | (2006.01) |
| *C12N 9/16* | (2006.01) |
| *C12N 9/10* | (2006.01) |
| *A61P 3/00* | (2006.01) |
| *C12N 9/24* | (2006.01) |
| *A61K 47/34* | (2017.01) |

(52) U.S. Cl.
CPC ............ *C12N 11/04* (2013.01); *A61K 9/0019* (2013.01); *A61K 9/0024* (2013.01); *A61K 47/10* (2013.01); *A61K 47/34* (2013.01); *A61K 47/6903* (2017.08); *A61M 5/178* (2013.01); *A61P 3/00* (2018.01); *C12N 9/1029* (2013.01); *C12N 9/16* (2013.01); *C12N 9/2402* (2013.01); *C12Y 301/06004* (2013.01); *C12Y 301/06012* (2013.01); *C12Y 301/06013* (2013.01); *C12Y 302/0102* (2013.01); *C12Y 302/0105* (2013.01); *C12Y 302/01023* (2013.01); *C12Y 302/01035* (2013.01); *C12Y 302/01045* (2013.01); *C12Y 302/01076* (2013.01); *C12Y 302/01139* (2013.01)

(58) Field of Classification Search
CPC combination set(s) only.
See application file for complete search history.

(56) References Cited

U.S. PATENT DOCUMENTS 7,968,085 B2 *   6/2011   Hersel ............... B82Y 5/00
                                                424/78.27

OTHER PUBLICATIONS

Lee, J. Biomaterials Research 2018 22 pp. 1-14.*
Jain, E. et al. Molec. Gen Metab 2017, vol. 120, p. s70, abstr 155.*
Asano et al., Observation of optomechanical coupling in a microbottle resonator; 23-pages.
Baaske et al., Optical observation of single atomic ions interacting with plasmonic nanorods in aqueous solution; Nature Photonics, 2016, vol. 10, No. 11, pp. 733-739.
Baaske et al., Single-molecule nucleic acid interactions monitored on a label-free microcavity biosensor platform; Nature Nanotechnology, Supplementary Information; 2014, 21-pages.
Baselga et al., Polyacrylamide Gels. Process of Network Formation; Eur. Polym. J.,1989, vol. 25, No. 5, pp. 477-480.
Calvet et al., Rheological Monitoring of Polyacrylamide Gelation: Importance of Cross-Link Density and Temperature; Macromolecules, 2004, vol. 37, pp. 7762-7771.
Denisin et al., Tuning the Range of Polyacrylamide Gel Stiffness fro Mechanobiology Application; ACS Appl. Mater. Interfaces, 2016, vol. 8, 21893.
Dasgupta et al., Microrheology of polyethylene oxide using diffusing wave spectroscopy and single scattering; Physical Review E., vol. 65, 10-pages.
Grabowski et al., Taliglucerase alfa: An enzyme replacement therapy using plant cell expression technology; Molecular Genetics and Metabolism; 2014, vol. 112, pp. 1-8.
He et al., Detecting single viruses and nanoparticles using whispering gallery microlasers; Nature Nanotechnology; 2011, 40-pages.
He et al., Production of α-L-iduronidase in maize for the potential treatment of a human lysosomal storage disease; Nature Communications; 2012, 9-pages.
He et al., Characterization and downstream mannose phosphorylation of human recombinant a-L-iduronidase produced in *Arabidopsis* complex glycan-deficient (cgl) seeds; Plant Biotechnology Journal; 2013, vol. 11, pp. 1034-1043.
Heylman et al., Optical microresonators as single-particle absorption spectrometer; Nat. Photonics, 2016, vol. 10, 788-796.
Junge et al., Strong coupling between single atoms and non-transversal photons; 7-pages.
Jung et al., Production and characterization of recombinant human acid a-glucosidase in transgenic rice cell suspension culture; Journal of Biotechnology; 2016, vol. 226, pp. 44-53.
Kjoniksen et al., Effects of Polymer Concentration and Cross-Linking Density on Rheology of Chemically Cross-Linked Poly-(vinyl alcohol) near the Gelation Threshold; Macromolecules, 1996, vol. 29, pp. 5215-5222.
Machavaram et al., Multi-point monitoring of cross-linking reactions; University of Birmingham; Applied Polymer Science; 2014; 12-pages.
Naghash et al., Formation and Structure of Polyacrylamide Gels; Journal of Applied Polymer Science, 1996, vol. 60, pp. 971-979.
Needleman-Wunsch algorithm for DNA sequence alignment (2 sequences).

(Continued)

*Primary Examiner* — Heidi Reese
(74) *Attorney, Agent, or Firm* — Stinson LLP (57) ABSTRACT

Compositions and methods for delivering enzymes in enzyme hydrogel formulations are disclosed. More particularly, the present disclosure relates to injectable enzyme hydrogel formulations and delivery of injectable enzyme hydrogel formulations. Also disclosed are methods for GALNS enzyme replacement therapy and lysosomal enzyme replacement therapy.

18 Claims, 6 Drawing Sheets
(6 of 6 Drawing Sheet(s) Filed in Color)
Specification includes a Sequence Listing.

(56) References Cited

OTHER PUBLICATIONS

Norisuye et al., Ultrasonic Investigation of the Gelation Process of Poly(Acrylamide) Gels; Macromol. Symp., 2006, vol. 242, pp. 208-215.
Pearson et al., Improved tools for biological sequence comparison, Proc. Natl. Acad. Sci., 1988, vol. 85, pp. 2444-2448.
Shao et al., Detection of Single Nanoparticles and Lentiviruses Using Microcavity Resonance Broadening; Advances Materials; 2013, 5-pages.
Smith-Waterman, Bioinformatics explained; 2007, 9-pages.
Solon et al., Fibroblast Adaptation and Stiffness Matching to Soft Elastic Substrates; Biophysical Journal, vol. 93, 2007, pp. 4453-4461.
Su et al., Label-free detection of single nanoparticles and biological molecules using microtoroid optical resonators; Light: Science & Applications; 2016, vol. 5, e16001 (6-pages).
Wen et al., Interplay of Matrix Stiffness and Protein Tethering in Stem Cell Differentiation; Nat Mater, 2014, vol. 13, No. 10, pp. 979-987.
Kizilay et al., Effect of hydrolysis on spatial inhomogeneity in poly(acrylamide) gels of various crosslink densities; Polymer; 2003, vol. 44, pp. 5239-5250.
Yeung et al., Effects of Substrate Stiffness on Cell Morphology, Cytoskeletal Structure, and Adhesion; Cell Motility and the Cytoskeleton, 2005, vol. 60, pp. 24-34.
Zhang et al., An investigation of a fiber optic sensor in the composite cure porcess; Smark Materials and Structures, 1999, vol. 8, pp. 515-518.

\* cited by examiner

DELIVERING ENZYME USING AN INJECTABLE HYDROGEL DEPOT

CROSS REFERENCE TO RELATED APPLICATIONS

This application claims priority to U.S. provisional patent application Ser. No., filed on Nov. 2, 2017, the disclosure of which is hereby incorporated by reference in its entirety.

STATEMENT IN SUPPORT FOR FILING A SEQUENCE LISTING

A paper copy of the Sequence Listing and a computer readable form of the Sequence Listing containing the file named "SLU17-008_ST25.txt", which is 4,838 bytes in size (as measured in MICROSOFT WINDOWS® EXPLORER), are provided herein and are herein incorporated by reference. This Sequence Listing consists of SEQ ID NO:1.

BACKGROUND OF THE DISCLOSURE

The present disclosure relates generally to enzyme hydrogel formulations and delivery systems using enzyme hydrogel formulations. More particularly, the present disclosure relates to a delivery system for delivering enzyme hydrogel formulations for sustained delivery of enzymes and methods for delivering enzymes using enzyme hydrogel formulations.

GALNS (also known as N-acetylgalactosamine 6-sulfate sulfatase; EC 3.1.6.4) is involved in the breakdown of glycosaminoglycans (GAGs) or mucopolysaccharides. Mutations in the GALNS gene cause Mucopolysaccharidosis type IV A (MPS IV, Morquio A disease, OMIM 253000) that reduces or eliminates the function of N-acetylgalactosamine 6-sulfate sulfatase. The lack of GALNS activity leads to the accumulation of keratan sulfate and chondroitin 6 sulfate within lysosomes. MPS IV A patients are characterized by short stature, hypoplasia of the odontoid process, pectus carinatum, kyphoscoliosis, genu valgum, laxity of joints, and corneal clouding, without central nervous system impairment. MPS IV A patients are generally treated through non-steroidal anti-inflammatory drugs, antibiotics, oxygen supplementation, orthopedic surgical procedures, and hematopoietic stem cell transplantation. Enzyme replacement therapy for Morquio A disease has been approved in the United States and Europe using recombinant GALNS (Elosulfase alfa-VIMIZIM®). Patients currently receive a 2.0 mg/kg/week dose.

Currently GALNS is delivered to patients via a several hour weekly infusions. The half-life ($t_{1/2}$) of GALNS enzyme in circulation is only 2.9 minutes. Because of the short half-life of the enzyme, GALNS must be delivered weekly to patients via a several hour infusion.

Accordingly, there exists a need to develop alternative compositions and methods for enzyme replacement therapy (ERT).

BRIEF DESCRIPTION OF THE DISCLOSURE

The present disclosure relates generally to enzyme hydrogel formulations and delivery systems using enzyme hydrogel formulations. More particularly, the present disclosure relates to a delivery system for delivering enzyme hydrogel formulations for sustained delivery of enzymes and methods for delivering enzymes using enzyme hydrogel formulations. The present disclosure also relates to a delivery system for delivering a GALNS hydrogel formulation for sustained delivery of GALNS and methods for delivering GALNS. Also disclosed are delivery systems for delivering an injectable lysosomal enzyme hydrogel formulation and methods for treating lysosomal diseases.

In one aspect, the present disclosure is directed to a delivery system for delivering an enzyme hydrogel formulation comprising: an applicator and an enzyme hydrogel formulation, the enzyme hydrogel comprising an enzyme, a polymer, and a buffer solution.

In one aspect, the present disclosure is directed to a method for delivering an enzyme hydrogel formulation, the method comprising: preparing an injectable enzyme hydrogel formulation, the injectable enzyme hydrogel formulation comprising an enzyme, a polymer, and a buffer solution; introducing the enzyme hydrogel formulation into an applicator.

In one aspect, the present disclosure is directed to a delivery system for delivering a GALNS hydrogel formulation comprising: an applicator and a GALNS hydrogel formulation, the GALNS hydrogel comprising GALNS, a polymer, and a buffer solution.

In one aspect, the present disclosure is directed to a method for delivering GALNS, the method comprising: preparing an injectable GALNS hydrogel formulation, the injectable GALNS hydrogel formulation comprising GALNS, a polymer, and a buffer solution; introducing the GALNS hydrogel formulation into an applicator.

In another aspect, the present disclosure is directed to a method for GALNS enzyme replacement therapy in an individual in need thereof, the method comprising administering to the individual in need an injectable GALNS hydrogel composition, the injectable GALNS hydrogel composition comprising GALNS, a polymer, and a buffer.

In another aspect, the present disclosure is directed to a delivery system for delivering an injectable lysosomal enzyme hydrogel formulation.

In another aspect, the present disclosure is directed to a method for treating a lysosomal enzyme disease in an individual in need thereof, the method comprising administering to the individual in need an injectable lysosomal enzyme hydrogel composition, the injectable lysosomal enzyme hydrogel composition comprising a lysosomal enzyme, a polymer, and a buffer.

BRIEF DESCRIPTION OF THE DRAWINGS

The patent or patent application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

FIGS. 2A and 2B are graphs depicting enzyme activity of rhGALNS enzyme dissolved in various solvents containing components of: (FIG. 2A) the PEG hydrogel and (FIG. 2B) the buffers and solvents used to prepare stock solutions and the injectable PEG hydrogel.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Delivery System for an Injectable GALNS Hydrogel Formulation

In one aspect, the present disclosure is directed to a delivery system for delivering a GALNS hydrogel formulation. The delivery system includes an applicator and a GALNS hydrogel formulation, the GALNS hydrogel comprising GALNS, a polymer, and a buffer solution.

In one particularly suitable embodiment, the delivery system includes an injectable GALNS hydrogel formulation administered using an applicator. A particularly suitable applicator is a syringe. Typically, the syringe includes a standard tubular design. It is particularly suitable that the tubular member of the syringe be made of a non-reactive clear or dark plastic to enable the operator of the syringe to visually monitor the amount of formulation within the tubular member. The tubular member is fitted with a plunger slidably received therein so that the inside walls of the tube and the outer edge of the plunger produce a tight fit around the circumference of the plunger.

Typically, the total volume of the syringe is from about 0.5 ml to about 2.0 ml and including from about 0.8 ml to about 1.4 ml. Further, the syringe has a diameter ranging from about 3 mm to about 5 mm and including about 4 mm.

Injectable GALNS hydrogel formulations are prepared by making a hydrogel polymer precursor solution by mixing a polymer and buffer solution. GALNS is then added to the hydrogel polymer precursor solution. To initiate polymerization of the polymer to form a hydrogel, a crosslinker is added to the hydrogel polymer precursor solution. Prior to gelation (i.e., hydrogel formation) of the hydrogel polymer precursor solution, the hydrogel polymer precursor solution is introduced to an applicator. The hydrogel polymer precursor solution can be introduced to the applicator by pipetting the hydrogel polymer precursor solution into the applicator or drawing the hydrogel polymer precursor solution into the applicator using a plunger. The injectable GALNS hydrogel formulation is then administered when the hydrogel polymer precursor solution begins becoming viscous. Viscosity of the hydrogel polymer precursor solution can be monitored by introducing a portion of the hydrogel polymer precursor solution into a container (in addition to the applicator) such as a microcentrifuge tube.

As known to those skilled in the art, the components forming the injectable GALNS hydrogel formulation can be sterilized. For example, the polymer precursor solution (with or without added GALNS and before or after initiating polymerization) can be filter sterilized.

Suitable final polymer concentrations of the hydrogel can range from about 5% (w/v) to about 20% (w/v). A particularly suitable polymer concentration of the final polymer concentration of the hydrogel can be about 10%. As known to those skilled in the art a stock solution of the polymer can be prepared and combined with other solutions to reach the final concentration.

The hydrogel precursor solution includes a polymer. The polymer precursor solution also includes a suitable buffer solution. Suitable polymers can be multiarm polymers and linear polymers. Suitable polymers can be polymers with end groups including acrylates (Ac), methyacryaltes (MA), vinyl sulfones (VS), terminal double bond moieties, and combinations thereof. Suitable polymers can be polyethylene glycol (PEG), polyethylene glycol acrylate (PEGAc), poly(glycolic acid) (PGA), poly(L-lactic acid) (PLA), poly(lactide-co-glycolide) (PLGA), poly(L-lactide) (PLLA), poly(D,L-lactide) (p(DLLA)), poly(ethylene glycol)1-co-poly(L-lactide) (PEG-PLLA), poly(ε-caprolactone (PCL), poly(L-lactide-co-ε-caprolactone) (P(LLA-CL)), poly(ε-caprolactone-co-ethyl ethylene phosphate (P(CL-EEP)), poly(ethylene-co-vinyl alcohol), poly(ethylenimine), polymethylmethacrylate (PMMA), hyaluronic acid, chitosan, pluronics, polyacrylamide, poly(vinyl alcohol) (PVA), polyhydroxyethylmethacrylate (polyHEMA), and combinations thereof. Suitable double bond terminated polyethylene glycols can be linear, 3-arm, 4-arm, 6-arm, and 8-arm. As known to one skilled in the art, the polymer can initially be mixed in a solution to form a stock polymer solution that is diluted to its final polymer concentration.

Suitable polymer concentrations of the hydrogel precursor solution can range from about 3% w/v to about 40% w/v. A particularly suitable final polymer concentration in the injectable hydrogel composition is about 10% w/v. Suitable pH of the hydrogel precursor solution can range from about 6.0 to about 8.5. A particularly suitable pH of the hydrogel precursor solution is about 7.4.

Suitable GALNS is recombinant GALNS. Particularly suitable GALNS is recombinant human GALNS. GALNS can have a nucleotide sequence of SEQ ID NO:1 (GALNS gene NG_008667.1; Gene ID:2588). A suitable GALNS can have a nucleotide sequence at least 80%, at least 85%, at least 90%, at least 91%, at least 92%, at least 93%, at least 94%, at least 95%, at least 96%, at least 97%, at least 98%, or at least 99% identical to GALNS gene (NG_008667.1; Gene ID:2588). Other suitable GALNS include SUMF1-GALNS, tagged E6-GALNS, E6-SUMF1 GALNS (as described in Tomatsu et al. 2010. Mol. Ther. 18(6):1094-1102), D6-D10 GALNS, and E6-E10 GALNS.

Percent identity of two sequences can be determined by aligning the sequences for optimal comparison. For example, gaps can be introduced in the sequence of a first nucleic acid sequence for optimal alignment with the second nucleic acid sequence. The same can be done for optimal alignment of amino acid sequences. The nucleotides or amino acid residues at corresponding positions are then compared. When a position in the first sequence is occupied by the same nucleotide or amino acid as at the corresponding position in the second sequence, the nucleic acids or amino acids are identical at that position. The percent identity between the two sequences is a function of the number of identical nucleotides or amino acids shared by the sequences. Hence, percent identity=[number of identical nucleotides/total number of overlapping positions]×100 or percent identity=[number of identical amino acids/total number of overlapping positions]×100. The percentage of sequence identity can be calculated according to this formula by comparing two optimally aligned sequences being compared, determining the number of positions at which the identical nucleic acid or amino acid occurs in both sequences to yield the number of matched positions (the "number of identical positions" in the formula above), dividing the number of matched positions by the total number of positions being compared (the "total number of overlapping positions" in the formula above), and multiplying the result by 100 to yield the percent sequence identity. In this comparison, the sequences can be the same length or may be different in length. Optimal alignment of sequences for determining a comparison window can be conducted by the local homology algorithm of Smith and Waterman (1981), by the homology alignment algorithm of Needleman and Wunsh (1972), by the search for similarity via the method of Pearson and Lipman (1988), by computerized implementations of these algorithms (GAP, BESTFIT, FASTA and TFASTA in the Wisconsin Genetics Software Package Release 7.0, Genetic Computer Group, 575, Science Drive, Madison, Wis.), or by inspection.

GALNS can have an amino acid sequence of SEQ ID NO:1 (GALNS protein NP_000503.1). A suitable GALNS can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:1.

Recombinant GALNS can be prepared in mammalian cells, plant cells, and microorganism cells. Suitable cells include Chinese Hamster Ovary cells, *Escherichia coli* cells, *Saccharomyces cerevisiae* cells, *Pichia pastoris* (reclassified as *Komagataella pastoris*) cells, *Yarrowia lipolytica* cells, *Ogataea minuta* cells and plant cells (as described in Grabowski et al. 2014, Molecular Genetics and Metabolism 112:1-8; He et al. 2013, Plant Biotechnology Journal 11:1034-1043; He et al. 2012, Nature Communications D01:10.1038; and Jung et al. 2016, Journal of Biotechnology 226:44-53; each of which is incorporated by reference in its entirety).

As known to one skilled in the art, GALNS can initially be mixed in a solution to form a stock GALNS solution that is diluted to its final dosage. Suitable GALNS dosage can range from about 100 Units/g/week to about 1000 Units/g/week. A particularly suitable dosage is about 250 units/gram of body weight. Suitable GALNS dosage can range from about 0.5 mg/kg of body weight per week (mg/kg/week) to about 4 mg/kg of body weight per week (mg/kg/week). As used herein, one unit refers to the amount of enzyme to catalyze the release of 1 nmol of substrate per hour.

The GALNS hydrogel formulation can further include a crosslinker. Suitable crosslinkers can be thiol-terminated polymers, small molecules, cysteine-terminated oligopeptides, cysteine-terminated polypeptides, and combinations thereof. Particularly suitable crosslinkers can be multithiol crosslinkers. Particularly suitable multithiol crosslinkers can be, for example, dithiothreitol (DTT), polyethylene glycol thiols (including for example, 3-arm, 4-arm, 6-arm, or 8-arm), polyethylene glycol thioglycolate (including for example, linear, 3-arm, 4-arm, 6-arm, or 8-arm), polyethylene glycol thiopropionate (including for example, 3-arm, 4-arm, 6-arm, or 8-arm), glycol dimercaptoacetate (GDMA), glycol di(3-mercaptopropionate) (GDMP), glyceryl dithioglycolate (GDT), tris[2-(3-mercaptopropionyloxy)ethyl]isocyanurate, pentaerythritol tetra-3-mercaptopropionate, ethoxilated-trimethylolpropan tri-3-mercaptopropionate, 2,2'-(Ethylenedioxy) diethanethiol (EDDT), Tetraethylene glycol dithiol (TEGDT), (S)-2 aminobutane 1, 4 dithiol (DTBA) and other thiol terminated molecules and cysteine containing oligo- and polypeptides.

Suitable buffers include HEPES buffer (e.g., 0.1M, pH 7.4), phosphate buffered saline, Tris buffered saline, and water, for example.

Suitable routes of administration include, for example, intraperitoneal (i.p.) parenteral, subcutaneous, intra-articular, intravenous, intramuscular, and inhaled.

In another aspect, the present disclosure is directed to a method for delivering GALNS. The method includes preparing an injectable GALNS hydrogel formulation, the injectable GALNS hydrogel formulation comprising GALNS, a polymer, and a buffer solution; introducing the GALNS hydrogel formulation into an applicator; and administering the GALNS hydrogel formulation to an individual.

The injectable GALNS hydrogel formulation is prepared as described herein. Suitable GALNS includes human GALNS and recombinant GALNS as described herein. Particularly suitable GALNS is recombinant human GALNS as described herein.

Suitable polymers are described herein. Suitable polymer concentration (w/v) ranges are described herein.

Suitable buffers are described herein including water, HEPES, phosphate buffered saline, tris buffered saline, and combinations thereof.

The injectable GALNS hydrogel formulation can further include a crosslinker as described herein.

Suitable routes of administration include, for example, intraperitoneal (i.p.) parenteral, subcutaneous, intra-articular, intravenous, intramuscular, oral and inhaled.

Methods of GALNS Enzyme Replacement Therapy in an Individual in Need Thereof by Administering a Hydrogel Composition Including GALNS In another aspect, the present disclosure is directed to a method of GALNS enzyme replacement therapy in an individual in need thereof. The method includes administering a hydrogel composition including GALNS.

Suitable GALNS dosage can range from about 100 Units/g/week to about 1000 Units/g/week. A particularly suitable dosage is about 250 units/gram of body weight. Suitable GALNS dosage can range from about 0.5 mg/kg of body weight per week (mg/kg/week) to about 4 mg/kg of body weight per week (mg/kg/week).

Suitable routes of administration include, for example, intraperitoneal (i.p.) parenteral, subcutaneous, intra-articular, intravenous, and intramuscular.

As used herein, "individual in need thereof" refers to an individual susceptible to or at risk of a specified disease, disorder, or condition. More particularly, in the present disclosure the methods of GALNS enzyme replacement therapy can be used with an individual or subset of individuals who have, are susceptible to, and at elevated risk for Morquio A.

Delivery System for an Injectable Lysosomal Enzyme Hydrogel Formulation

In one aspect, the present disclosure is directed to a delivery system for delivering an injectable lysosomal enzyme hydrogel formulation. The delivery system includes an applicator and a lysosomal enzyme hydrogel formulation, the lysosomal enzyme hydrogel comprising a lysosomal enzyme, a polymer, and a buffer solution.

Suitable lysosomal enzymes include α-L-iduronidase, Iduronate-2-sulfate sulfatase, Heparan N sulfatase, α-N-acetylglucosaminidase, acetyl-CoA: α-glucosaminide acetyltransferase, N-acetylglucosamine 6-sulfatase, β-galactosidase, Arylsulfatase B, β-Glucuronidase Hyaluronidase, acid α-glucosidase, glucocerebrosidase, etc.

In one particularly suitable embodiment, the delivery system includes an injectable lysosomal enzyme hydrogel formulation administered using an applicator. A particularly suitable applicator is a syringe as described herein.

Typically, the total volume of the syringe is from about 0.5 ml to about 2.0 ml and including from about 0.8 ml to about 1.4 ml as described herein. Further, the syringe has a diameter ranging from about 3 mm to about 5 mm and including about 4 mm as described herein.

Injectable lysosomal enzyme hydrogel formulations are prepared by making a hydrogel polymer precursor solution by mixing a polymer and buffer solution as described herein. The lysosomal enzyme is then added to the hydrogel polymer precursor solution. To initiate polymerization of the polymer to form a hydrogel, a crosslinker is added to the hydrogel polymer precursor solution. Prior to gelation (i.e., hydrogel formation) of the hydrogel polymer precursor solution, the hydrogel polymer precursor solution is introduced to an applicator. The hydrogel polymer precursor solution can be introduced to the applicator by pipetting the hydrogel polymer precursor solution into the applicator or drawing the hydrogel polymer precursor solution into the applicator using a plunger. The injectable lysosomal enzyme hydrogel formulation is then administered when the hydrogel polymer precursor solution begins becoming viscous. Viscosity of the hydrogel polymer precursor solution can be monitored by introducing a portion of the hydrogel polymer precursor solution into a container (in addition to the applicator) such as a microcentrifuge tube.

As known to those skilled in the art, the components forming the injectable lysosomal enzyme hydrogel formulation can be sterilized. For example, the polymer precursor solution (with or without added lysosomal enzyme and before or after initiating polymerization) can be filter sterilized.

Suitable final polymer concentrations of the hydrogel can range from about 5% (w/v) to about 20% (w/v) as described herein. A particularly suitable polymer concentration of the final polymer concentration of the hydrogel can be about 10%. As known to those skilled in the art a stock solution of the polymer can be prepared and combined with other solutions to reach the final concentration.

The hydrogel precursor solution includes a polymer. The polymer precursor solution also includes a suitable buffer solution. Suitable polymers can be multiarm polymers and linear polymers as described herein. Suitable polymers can be polymers with end groups including acrylates (Ac), methyacryaltes (MA), vinyl sulfones (VS), terminal double bond moieties, and combinations thereof. Suitable polymers can be polyethylene glycol (PEG), polyethylene glycol acrylate (PEGAc), poly(glycolic acid) (PGA), poly(L-lactic acid) (PLA), poly(lactide-co-glycolide) (PLGA), poly(L-lactide) (PLLA), poly(D,L-lactide) (p(DLLA)), poly(ethylene glycol)1-co-poly(L-lactide) (PEG-PLLA), poly(ε-caprolactone (PCL), poly(L-lactide-co-ε-caprolactone) (P(LLA-CL)), poly(ε-caprolactone-co-ethyl ethylene phosphate (P(CL-EEP)), poly(ethylene-co-vinyl alcohol), poly(ethylenimine), polymethylmethacrylate (PMMA), hyaluronic acid, chitosan, pluronics, polyacrylamide, poly(vinyl alcohol) (PVA), polyhydroxyethylmethacrylate (poly-HEMA), and combinations thereof. Suitable double bond terminated polyethylene glycols can be linear, 3-arm, 4-arm, 6-arm, and 8-arm. As known to one skilled in the art, the polymer can initially be mixed in a solution to form a stock polymer solution that is diluted to its final polymer concentration.

Suitable polymer concentrations of the hydrogel precursor solution can range from about 3% w/v to about 40% w/v as described herein. A particularly suitable final polymer concentration in the injectable hydrogel composition is about 10% w/v. Suitable pH of the hydrogel precursor solution can range from about 6.0 to about 8.5. A particularly suitable pH of the hydrogel precursor solution is about 7.4.

Methods for Treating Lysosomal Diseases

In another aspect, the present disclosure is directed to a method for treating a lysosomal enzyme disease in an individual in need thereof, the method comprising administering to the individual in need an injectable lysosomal enzyme hydrogel composition, the injectable lysosomal enzyme hydrogel composition comprising a lysosomal enzyme, a polymer, and a buffer.

Suitable lysosomal enzymes include α-L-iduronidase, Iduronate-2-sulfate sulfatase, Heparan N sulfatase, α-N-acetylglucosaminidase, acetyl-CoA: α-glucosaminide acetyltransferase, N-acetylglucosamine 6-sulfatase, β-galactosidase, Arylsulfatase B, β-Glucuronidase, Hyaluronidase, acid α-glucosidase, glucocerebrosidase, etc.

Injectable lysosomal enzyme hydrogel formulations are prepared by making a hydrogel polymer precursor solution by mixing a polymer and buffer solution as described herein.

Lysosomal diseases include, for example, Mucopolysaccharidosis I (Hurler Disease), Mucopolysaccharidosis II (Hunter Disease), Mucopolysaccharidosis IIIA (Sanfilippo A), Mucopolysaccharidosis IIIB (Sanfilippo B) Mucopolysaccharidosis IIIC (Sanfilippo C) Mucopolysaccharidosis IIID (Sanfilippo D), Mucopolysaccharidosis IVA (Morquio A), Mucopolysaccharidosis IVB (Morquio B), Mucopolysaccharidosis VI (Maroteaux-Lamy), Mucopolysaccharidosis VII (Sly disease), Mucopolysaccharidosis IX (Natowicz Syndrome), Gaucher disease, Pompe disease, etc_and blood disorders.

The disclosure will be more fully understood upon consideration of the following non-limiting Examples.

EXAMPLES

Example 1

Materials and Methods

Polyethylene glycol tetra-acrylate (4-arm PEGAc) (10 kDa) was obtained from Jenkem Technology USA Inc. (Plano, Tex.). Polyethylene glycol dithiol (PEG-diSH) was purchased from Laysan Bio Inc. (Arab, A L). Hepes was purchased from Sigma Aldrich (St. Louis, Mo.).

To produce recombinant human GALNS, Chinese Hamster Ovary (CHO) cells were stably transfected with a mammalian expression vector containing recombinant human GALNS (rhGALNS) cDNA. The highest expressing clone was expanded and used to collect conditioned medium containing secreted rhGALNS to use as a source for purification. The rhGALNS was purified from the conditioned medium using a two-column procedure. Batches of medium containing the enzyme were filtered through 0.2 µm capsule filters (Pall Gelman). Filtered medium was adjusted to pH 5.5 with acetic acid and was concentrated 15-fold and then dialyzed against 25 mM sodium acetate and 1 mM β-glycerophosphate buffer (pH 5.5) using an Amicon stirred-cell ultrafiltration unit with a Millipore XM50 membrane. All the procedures were performed at 4° C. unless otherwise stated.

The concentrated and dialyzed medium containing rhGALNS was loaded onto a CM-sepharose CL-6B (Sigma, St. Louis, Mo.) column (15 cm×1.5 cm) equilibrated with 25 mM sodium acetate and 1 mM ß-glycerophosphate (pH 5.5) at flow rate of 25 ml per hour. Before elution of the bound proteins, the column was washed with 20 volumes of 25 mM sodium acetate and 1 mM β-glycerophosphate buffer (pH 5.5) at the same flow rate. The enzyme was eluted with 200 ml of a linear gradient of 0-0.1M NaCl, pH 5.5 at flow rate of 25 ml per hour. The fractions with GALNS activity were pooled and concentrated in Centricon centrifugal filters with YM-30 membranes (Millipore, Bedford, Mass.). The concentrated fractions were applied to a 400 ml Sephacryl S-300 HR (Amersham Biosciences) gel filtration column equilibrated with 25 mM sodium acetate, 1 mM β-glycerophosphate, and 100 mM NaCl at pH 5.5 (flow rate 25 ml per hour). The column was eluted with equilibration buffer. Fractions with high rhGALNS activity were pooled, concentrated, and analyzed under denaturing conditions by 10% SDS-PAGE gel. The gels were stained with silver staining (Sigma, St. Louis, Mo.). Aliquots of the purified and concentrated rhGALNS were assayed for enzyme activity using 4-methylumbelliferyl-β-D-galactopyranoside-6-sulfate as a substrate (Moscerdam Substrate, Rotterdam, The Netherlands).

rhGALNS enzyme activity was determined by incubating rhGALNS overnight at 37° C. in a reaction mixture of 4-methylumbelliferyl-β-D-galactopyranoside-6-sulfate as a substrate (Moscerdam Substrate, Rotterdam, The Netherlands). Activity was expressed as nanomoles of 4-methylumbelliferone released per milligram of protein per hour.

Injectable hydrogel formulations having hydrogels of 10% (w/v) polymer concentration were prepared by combining 4-arm PEGAc and PEG-diSH in a 1:1 molar ratio. A 20% (w/v) stock solution of 4-arm PEGAc was prepared. HEPES buffer (0.1M, pH 7.4) was pipetted in a microcentrifuge tube. 4-arm PEGAc was then added to the microcentrifuge tube and mixed gently by pipetting. rhGALNS enzyme was also added to the precursor solution and mixed gently again. Finally, a stock solution of PEG-diSH was prepared immediately prior to adding into the precursor solution to avoid prolonged exposure to water. The precursor solution was mixed well and pipetted into the barrel of a 1 mL syringe. A 0.22 µm filter was placed on the end of the syringe and the precursor solution was filtered into a sterile microcentrifuge tube. 100 µL precursor solution was then drawn into a 1 ml syringe. The remaining amount of precursor solution in the microcentrifuge tube was used to check the viscosity as the solution polymerized. Once the precursor solution started becoming viscous, the solution in the insulin syringe was injected (~20 min).

To determine rhGALNS release from hydrogels, the hydrogels were placed in a microcentrifuge tube with 200 µL of release buffer (buffer with 25 mM sodium acetate, 1 mM β-glycerophosphate pH 5.5, 100 mM NaCl) and placed at 37° C. with shaking. Hydrogels were prepared in triplicates for several time points: 3 hours, 1 day, 2 days, 3 days, 4 days, 5 days, 6 days, and 7 days. At each time point, all of the releasate was collected from each microcentrifuge tube and placed in −80° C. until further analysis. The releasates were analyzed for enzyme activity as described previously and for protein content using the Bradford assay following the manufacturer's protocol. Specific enzyme activity was calculated as enzyme activity divided by protein content for each sample.

To determine cumulative release, hydrogels were prepared in triplicates and placed in microcentrifuge tubes with 200 µL of release buffer (buffer with 25 mM sodium acetate, 1 mM β-glycerophosphate pH 5.5, 100 mM NaCl) and incubated at 37° C. with shaking. A 50 µL sample was taken at each time point listed in the previous section and replaced with 50 µL of fresh release buffer. The samples were immediately placed at −80° C. until further analysis. The releasates were analyzed for enzyme activity and for protein content using the Bradford assay. Specific enzyme activity was calculated as enzyme activity divided by protein content for each sample.

To determine the in vivo biodistribution of fluorescent labeled rhGALNS, 1 mg/ml of the purified rhGALNS enzyme was labeled with Alexa Fluor 488 Protein Labeling Kit following manufacturer's instruction (Thermo Fisher Scientific). Injectable hydrogels were prepared as previously described. Abdominal and thoracic region of C57B1 mice were shaved for in vivo imaging of fluorescent labeled rhGALNS. The labeled enzyme was injected into two C57B1 mice (8 weeks old) intraperitoneally (i.p.) at a dose of 250 units/g rhGALNS. One of the mice had labeled enzyme (i.p.), and another mouse had labeled enzyme encapsulated in microspheres (i.p.m). An additional mouse which was not injected was used as a control. All mice were imaged at 1 day, 2 days, 3 days and 4 days by using an IVIS Spectrum In Vivo Imaging System (Perkin Elmer).

Figure 1:
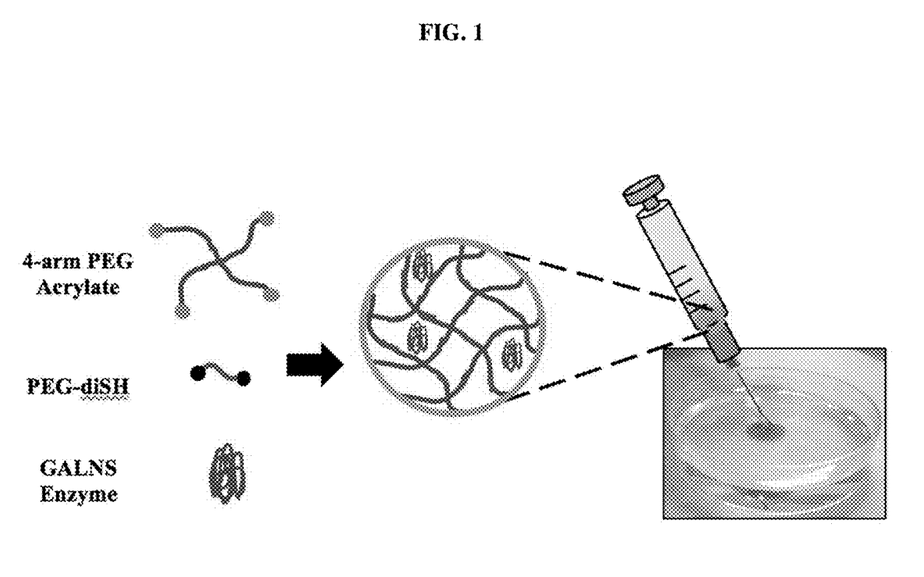
FIG. 1 is a schematic illustration of injectable polyethylene glycol (PEG) hydrogel depot loaded with recombinant human GALNS (rhGALNS) enzyme. As illustrated, rhGALNS enzyme is encapsulated in 4-arm PEG acrylate crosslinked with PEG dithiol via the Michael-type addition reaction forming an injectable hydrogel depot.

FIG. 1 is a schematic illustrating injectable polyethene glycol (PEG) hydrogel depot loaded with rhGALNS enzyme. rhGALNS enzyme is encapsulated in 4-arm PEG acrylate crosslinked with PEG dithiol via the Michael-type addition reaction forming an injectable hydrogel depot loaded with rhGALNS enzyme.

Figure 2A:
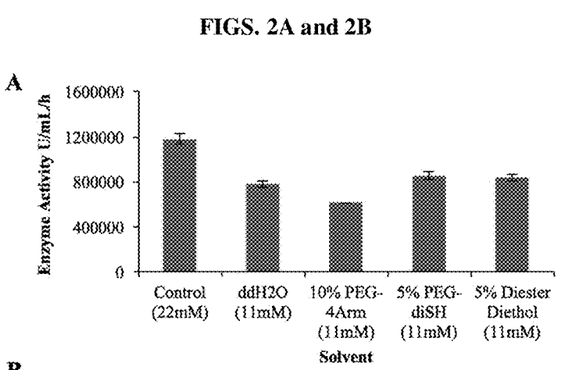
Figure 2B:
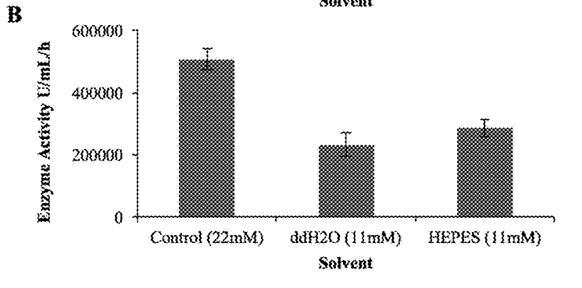

FIGS. 2A and 2B depict the enzyme activity of rhGALNS prepared in various solvents containing the polyethylene glycol (PEG) hydrogel (FIG. 2A) and (FIG. 2B) the buffers and solvents used to prepare stock solutions and the injectable PEG hydrogel. As shown in FIGS. 2A and 2B, the individual components of both the hydrogel and the buffers used to prepare the hydrogel had no adverse effects on the activity of the rhGALNS enzyme. ddH$_2$O (11 mM) was also a control that uses half of the concentration of the substrate.

Figure 3A:
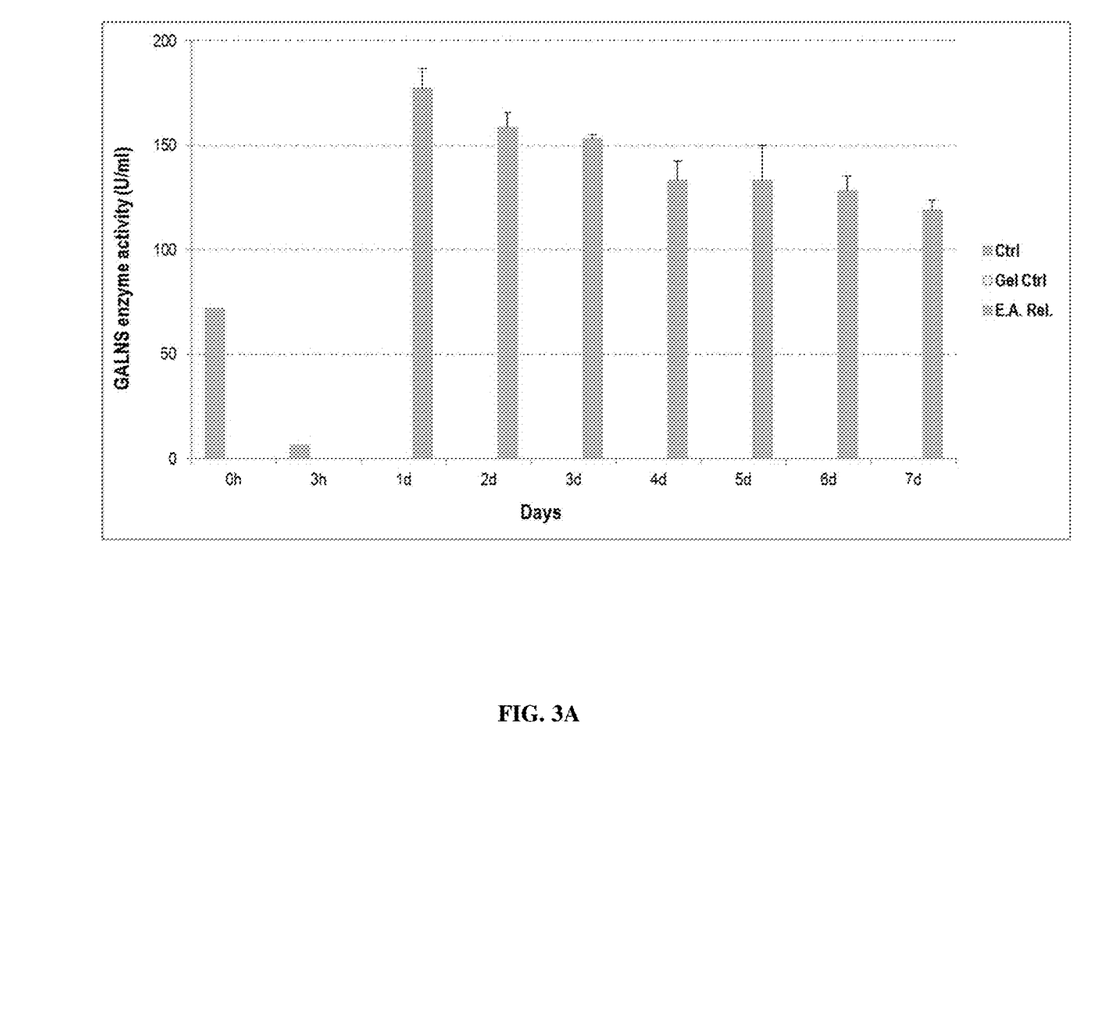
FIG. 3A is a graph depicting the enzyme activity of releasates collected from rhGALNS encapsulated hydrogels incubated at 37° C. over a period of 7 days (pink). The enzyme activity of rhGALNS enzyme incubated at 37° C. (blue) and a hydrogel without any enzyme (yellow) are also shown.
Figure 3B:
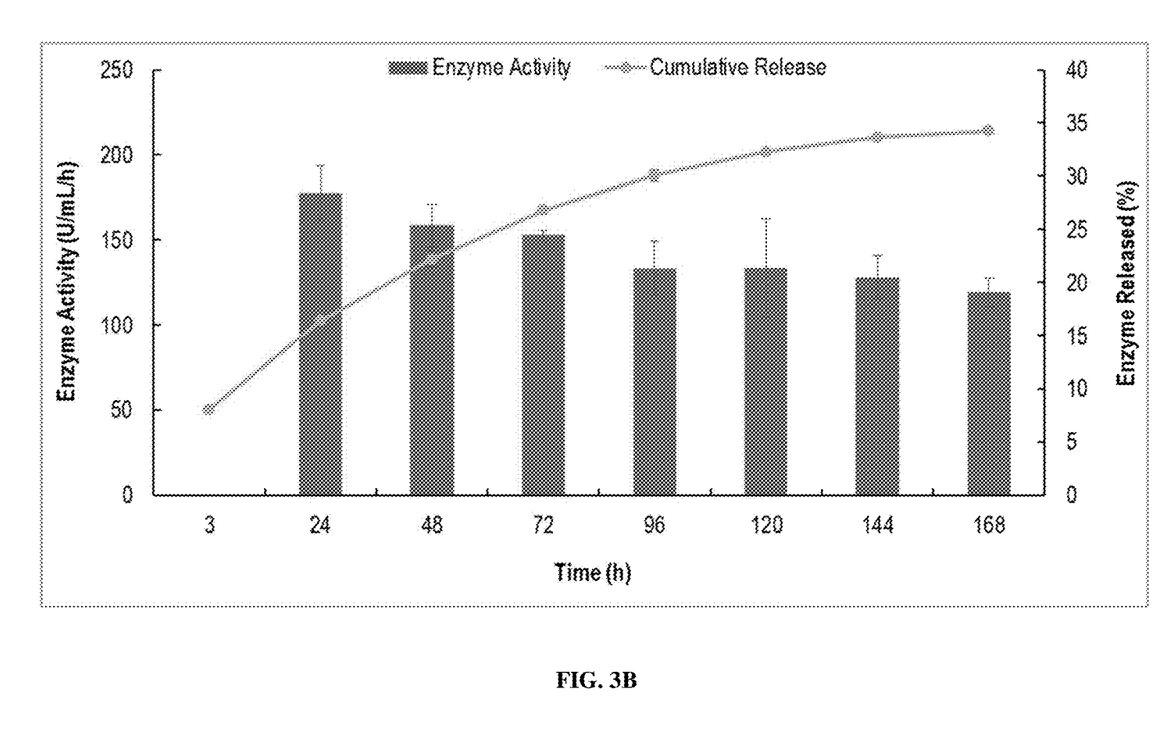
FIG. 3B compares enzyme activity of relesates collected from rhGALNS encapsulated hydrogels incubated at 37° C. over a period of 7 days (red) along with the cumulative release of rhGALNS from hydrogels (green), which shows the percent of enzyme released, over the same time period.

As shown in FIGS. 3A and 3B, GALNS activity was maintained for up to 7 days when encapsulated in a PEG hydrogel. Additionally, these results showed that the enzyme could have a sustained release throughout the 7 day incubation period.

Figure 4:
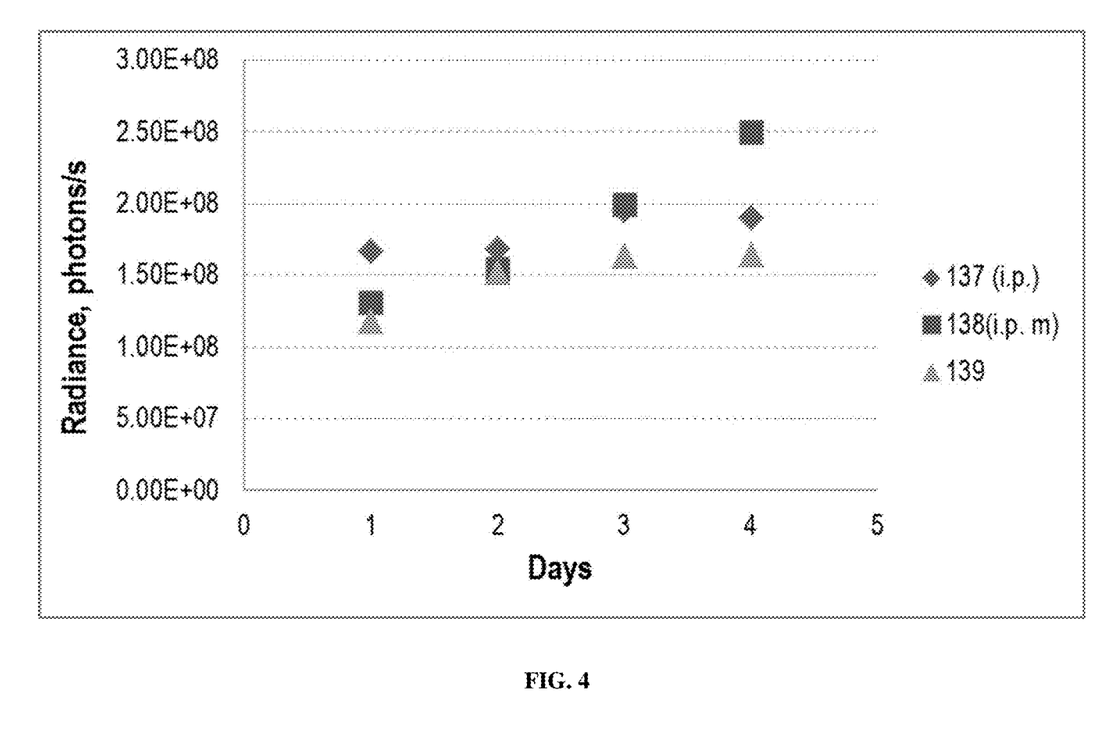
FIG. 4 is a graph depicting in vivo biodistribution of fluorescent labeled rhGALNS. (Blue) Mouse injected i.p. with rhGALNS. (Pink) Mouse injected i.p. with rhGALNS encapsulated within injectable gels. (Green) Control mouse not injected depicting the background signal.

As shown in FIG. 4, mice injected i.p. with the rhGALNS/PEG hydrogels (i.p.m.) had higher signal at day 4 than labeled rhGALNS. This demonstrated that the encapsulated enzyme was released slowly into the circulation when compared to non-encapsulated rhGALNS.

In this Example, the uptake of GALNS by Morquio deficient fibroblasts was determined.

Human primary GALNS deficient fibroblasts were plated and allowed to grow to confluence. GALNS enzyme was added to the media at a concentration 5,000 units/ml. After 5 h (green bar) or 24 h (gray bar) of incubation at 37° C., the media was removed, the cells were washed three times with 0.9% NaCl, and resuspended in 0.1 ml of 1% sodium deoxycholate. GALNS activity and protein were measured.

Figure 5:
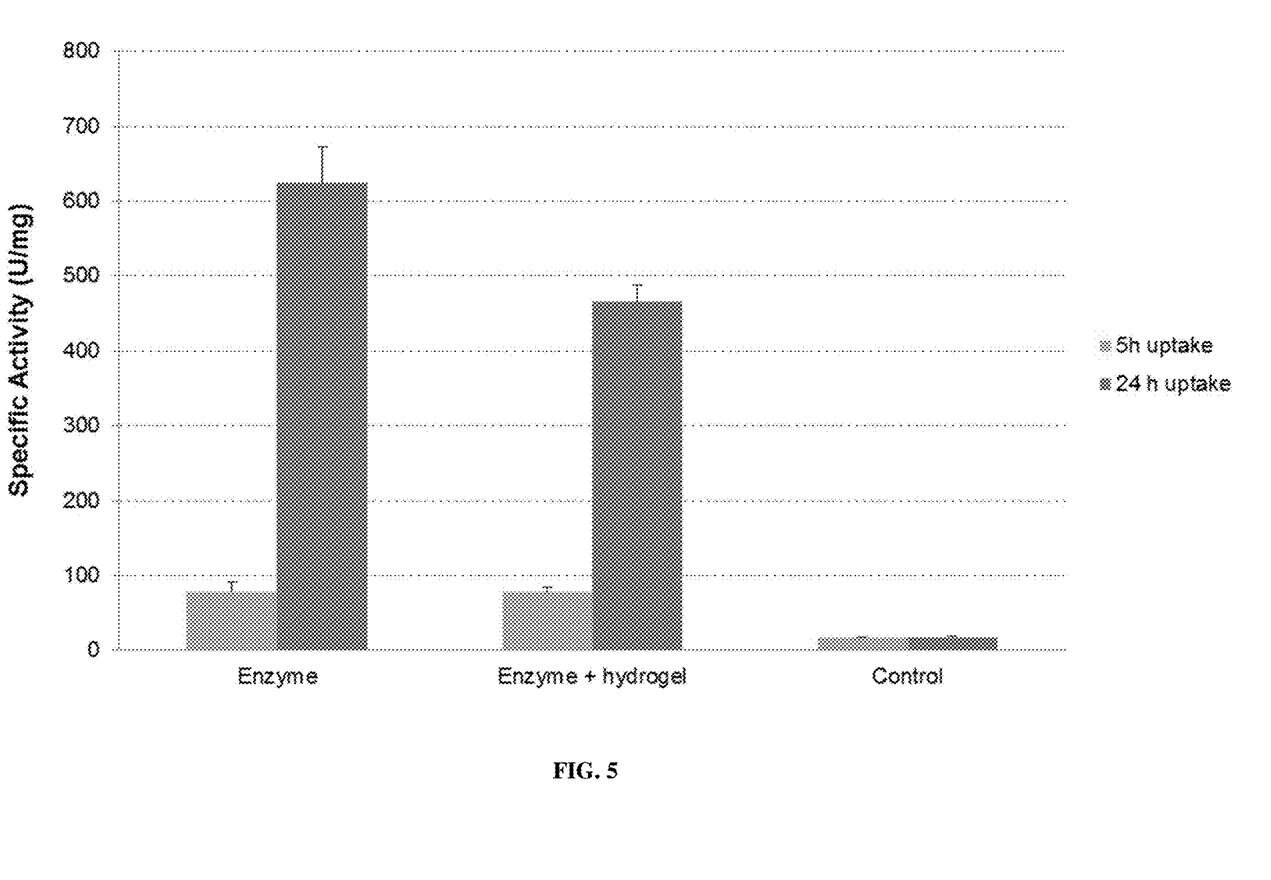
FIG. 5 is a graph depicting the uptake of GALNS by Morquio deficient fibroblasts. 5,000 units/ml of GALNS enzyme were added to the culture of deficient fibroblasts for 5 h (green) or 24 h (gray). Enzyme: GALNS enzyme added into the media of the fibroblasts; Enzyme+hydrogel: Encapsulated GALNS enzyme added to a transwell and exposed to the deficient fibroblasts; Control: No enzyme was added to the deficient fibroblasts.

As depicted in FIG. 5, both enzyme added into the media of the fibroblasts and encapsulated enzyme (Enzyme+hydrogel) can be uptaken by deficient fibroblasts at different time points. The encapsulation does not impede the release of the active GALNS enzyme and the uptake by deficient fibroblasts.

As disclosed in the present disclosure, the ability to encapsulate GALNS enzyme in injectable PEGAc hydrogels with sustained release is a new feature. The enzyme slowly releases over time, rather than releasing in a bolus dose when injected as a solution. The enzyme remains in the hydrogel for 7 days or more. In addition, the hydrogel protects the enzyme activity of the GALNS. As a solution, the enzyme loses significant activity in less than 24 hours. However, when encapsulated within the injectable PEGAc hydrogel depot, the enzyme retains activity for 7 days or more.

The benefits afforded by the compositions and methods disclosed herein include the use of a biocompatible, bio-inert, biodegradable material that can be used to encapsulate and release the GALNS enzyme in a sustained manner, while also preserving enzyme activity. The hydrogel is injectable for minimally invasive delivery and degradable with non-toxic and easily cleared degradation products (hence no device removal is necessary). The problem solved by this technique is that normally, the GALNS enzyme loses activity in about 3 hours when incubated at 37° C. and is eliminated by the body quickly. Hence, the current therapy involves weekly enzyme infusions that last for 6-8 hours. An advantage of the hydrogel compositions are that they allows the GALNS enzyme to retain activity and release in a sustained manner for up to 7 days; hence, a single injection can be used in place of multiple injections to provide a longer lasting benefit than current infusions.

What is claimed is:

1. A delivery system for delivering an enzyme hydrogel formulation comprising: an applicator and an enzyme hydrogel formulation, the enzyme hydrogel formulation comprising an enzyme selected from the group consisting of N-acetylgalactosamine 6-sulfate sulfatase (GALNS) and a lysosomal enzyme selected from the group consisting of Iduronate-2-sulfate sulfatase, Heparan N sulfatase, N-acetylglucosaminidase, acetyl-CoA: glucosaminide acetyltransferase, N-acetylglucosamine 6-sulfatase, Arylsulfatase B, Glucuronidase, acid glucosidase, and combinations thereof, a polymer, and a buffer solution, wherein the enzyme hydrogel formulation is not a microparticle.

2. The delivery system of claim 1, wherein the enzyme comprises a recombinant enzyme.

3. The delivery system of claim 1, wherein the enzyme comprises a human enzyme.

4. The delivery system of claim 1, wherein the polymer comprises polyethylene glycol (PEG), polyethylene glycol acrylate (PEGAc), poly(glycolic acid) (PGA), poly(L-lactic acid) (PLA), poly(lactide-co-glycolide) (PLGA), poly(L-lactide) (PLLA), poly(D,L-lactide) (p(DLLA)), poly(ethylene glycol)l-co-poly(L-lactide) (PEG-PLLA), poly(ε-caprolactone) (PCL), poly(L-lactide-co-ε-caprolactone) (P(LLA-CL)), poly(ε-caprolactone-co-ethyl ethylene phosphate (P(CL-EEP)), poly(ethylene-co-vinyl alcohol), poly(ethylenimine), polymethylmethacrylate (PMMA), hyaluronic acid, chitosan, pluronics, polyacrylamide, poly(vinyl alcohol) (PVA), polyhydroxyethylmethacrylate (polyHEMA), and combinations thereof.

5. The delivery system of claim 1, wherein the buffer comprises water, HEPES, phosphate buffered saline, tris buffered saline, and combinations thereof.

6. The delivery system of claim 1, wherein the applicator comprises a syringe.

7. The delivery system of claim 1 wherein the GALNS dosage range from about 0.5 mg/kg of body weight per week (mg/kg/week) to about 4 mg/kg of body weight per week (mg/kg/week).

8. A method for delivering an enzyme hydrogel formulation, the method comprising: preparing an injectable enzyme hydrogel formulation, the injectable enzyme hydrogel formulation comprising an enzyme, selected from the group consisting of N-acetylgalactosarnine 6-sulfate sulfatase (GALNS) and a lysosomal enzyme selected from the group consisting of Iduronate-2-sulfate sulfatase, Heparan N sulfatase, N-acetylglucosaminidase, acetyl-CoA: glucosaminide acetyltransferase, N-acetylglucosamine 6-sulfatase, Arylsulfatase B, Glucuronidase, add glucosidase, and combinations thereof, a polymer, and a buffer solution; introducing the enzyme hydrogel formulation into an applicator, wherein the enzyme hydrogel formulation is not a microparticle.

9. The method of claim 8, wherein the enzyme comprises a recombinant enzyme.

10. The method of claim 8, wherein the enzyme comprises a human enzyme.

11. The method of claim 8, wherein the enzyme is N-acetylgalactosamine 6-sulfate sulfatase (GALNS).

12. The method of claim 11, wherein the enzyme is a human recombinant N-acetylgalactosamine 6-sulfate sulfatase (GALNS).

13. The method of claim of claim 11, wherein the GALNS dosage range from about 0.5 mg/kg of body weight per week (mg/kg/week) to about 4 mg/kg of body weight per week (mg/kg/week).

14. The method of claim 8, wherein the enzyme is a lysosomal enzyme selected from the group consisting of α-L-iduronidase, Iduronate-2-sulfate sulfatase, Heparan N sulfatase, α-N-acetylglucosaminidase, acetyl-CoA: α-glucosaminide acetyltransferase, N-acetylglucosamine 6-sulfatase, β-galactosidase, Arylsulfatase B, β-Glucuronidase, Hyaluronidase, acid α-glucosidase, glucocerebrosidase, and combinations thereof.

15. The method of claim 8, wherein the polymer is chosen from polyethylene glycol (PEG), polyethylene glycol acrylate (PEGAc), poly(glycolic acid) (PGA), poly(L-lactic acid) (PLA), poly(lactide-co-glycolide) (PLGA), poly(L-lactide) (PLLA), poly(D,L-lactide) (p(DLLA)), poly(ethylene glycol)l-co-poly(L-lactide) (PEG-PLLA), poly(ε-caprolactone) (PCL), poly(L-lactide-co-ε-caprolactone) (P(LLA-CL)), poly(ε-caprolactone-co-ethyl ethylene phosphate (P(CL-EEP)), poly(ethylene-co-vinyl alcohol), poly(ethylenimine), polymethylmethacrylate (PMMA), hyaluronic acid, chitosan, pluronics, polyacrylamide, poly(vinyl alcohol) (PVA), polyhydroxyethylmethacrylate (polyHEMA), and combinations thereof.

16. The method of claim 15, wherein the polymer comprises 4-arm polyethylene glycol acrylate.

17. The method of claim 8, wherein the buffer comprises water, HEPES, phosphate buffered saline, tris buffered saline, and combinations thereof.

18. The method of claim 8, wherein the applicator comprises a syringe.

* * * * *

SEQUENCE LISTING

```
<160> NUMBER OF SEQ ID NOS: 1

<210> SEQ ID NO 1
<211> LENGTH: 522
<212> TYPE: PRT
<213> ORGANISM: Homo sapiens

<400> SEQUENCE: 1

Met Ala Ala Val Val Ala Ala Thr Arg Trp Trp Gln Leu Leu Leu Val
1               5                   10                  15

Leu Ser Ala Ala Gly Met Gly Ala Ser Gly Ala Pro Gln Pro Pro Asn
            20                  25                  30

Ile Leu Leu Leu Leu Met Asp Asp Met Gly Trp Gly Asp Leu Gly Val
        35                  40                  45

Tyr Gly Glu Pro Ser Arg Glu Thr Pro Asn Leu Asp Arg Met Ala Ala
    50                  55                  60

Glu Gly Leu Leu Phe Pro Asn Phe Tyr Ser Ala Asn Pro Leu Cys Ser
65                  70                  75                  80

Pro Ser Arg Ala Ala Leu Leu Thr Gly Arg Leu Pro Ile Arg Asn Gly
                85                  90                  95

Phe Tyr Thr Thr Asn Ala His Ala Arg Asn Ala Tyr Thr Pro Gln Glu
            100                 105                 110

Ile Val Gly Gly Ile Pro Asp Ser Glu Gln Leu Leu Pro Glu Leu Leu
        115                 120                 125

Lys Lys Ala Gly Tyr Val Ser Lys Ile Val Gly Lys Trp His Leu Gly
    130                 135                 140

His Arg Pro Gln Phe His Pro Leu Lys His Gly Phe Asp Glu Trp Phe
145                 150                 155                 160

Gly Ser Pro Asn Cys His Phe Gly Pro Tyr Asp Asn Lys Ala Arg Pro
                165                 170                 175

Asn Ile Pro Val Tyr Arg Asp Trp Glu Met Val Gly Arg Tyr Tyr Glu
            180                 185                 190
```

-continued

```
Glu Phe Pro Ile Asn Leu Lys Thr Gly Glu Ala Asn Leu Thr Gln Ile
            195                 200                 205

Tyr Leu Gln Glu Ala Leu Asp Phe Ile Lys Arg Gln Ala Arg His His
        210                 215                 220

Pro Phe Phe Leu Tyr Trp Ala Val Asp Ala Thr His Ala Pro Val Tyr
225                 230                 235                 240

Ala Ser Lys Pro Phe Leu Gly Thr Ser Gln Arg Gly Arg Tyr Gly Asp
                245                 250                 255

Ala Val Arg Glu Ile Asp Asp Ser Ile Gly Lys Ile Leu Glu Leu Leu
            260                 265                 270

Gln Asp Leu His Val Ala Asp Asn Thr Phe Val Phe Thr Ser Asp
            275                 280                 285

Asn Gly Ala Ala Leu Ile Ser Ala Pro Glu Gln Gly Gly Ser Asn Gly
    290                 295                 300

Pro Phe Leu Cys Gly Lys Gln Thr Thr Phe Glu Gly Gly Met Arg Glu
305                 310                 315                 320

Pro Ala Leu Ala Trp Trp Pro Gly His Val Thr Ala Gly Gln Val Ser
                325                 330                 335

His Gln Leu Gly Ser Ile Met Asp Leu Phe Thr Thr Ser Leu Ala Leu
            340                 345                 350

Ala Gly Leu Thr Pro Pro Ser Asp Arg Ala Ile Asp Gly Leu Asn Leu
        355                 360                 365

Leu Pro Thr Leu Leu Gln Gly Arg Leu Met Asp Arg Pro Ile Phe Tyr
    370                 375                 380

Tyr Arg Gly Asp Thr Leu Met Ala Ala Thr Leu Gly Gln His Lys Ala
385                 390                 395                 400

His Phe Trp Thr Trp Thr Asn Ser Trp Glu Asn Phe Arg Gln Gly Ile
                405                 410                 415

Asp Phe Cys Pro Gly Gln Asn Val Ser Gly Val Thr Thr His Asn Leu
                420                 425                 430

Glu Asp His Thr Lys Leu Pro Leu Ile Phe His Leu Gly Arg Asp Pro
            435                 440                 445

Gly Glu Arg Phe Pro Leu Ser Phe Ala Ser Ala Glu Tyr Gln Glu Ala
    450                 455                 460

Leu Ser Arg Ile Thr Ser Val Val Gln Gln His Gln Glu Ala Leu Val
465                 470                 475                 480

Pro Ala Gln Pro Gln Leu Asn Val Cys Asn Trp Ala Val Met Asn Trp
                485                 490                 495

Ala Pro Pro Gly Cys Glu Lys Leu Gly Lys Cys Leu Thr Pro Pro Glu
                500                 505                 510

Ser Ile Pro Lys Lys Cys Leu Trp Ser His
            515                 520
```